United States Patent
Ido et al.

(10) Patent No.: US 9,835,556 B2
(45) Date of Patent: Dec. 5, 2017

(54) GAS ANALYSIS DEVICE (71) Applicant: HORIBA, LTD., Kyoto (JP)

(72) Inventors: Takuya Ido, Kyoto (JP); Yasushi Hirata, Kyoto (JP); Toshiaki Nakagawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 15/366,054

(22) Filed: Dec. 1, 2016

(65) Prior Publication Data

US 2017/0082537 A1    Mar. 23, 2017

Related U.S. Application Data (63) Continuation of application No. PCT/JP2015/077795, filed on Sep. 30, 2015.

(30) Foreign Application Priority Data

Oct. 17, 2014    (JP) .................................. 2014-212310

(51) Int. Cl.
*G01J 5/02* (2006.01)
*G01N 21/55* (2014.01)
(Continued)

(52) U.S. Cl.
CPC ............. *G01N 21/55* (2013.01); *G01N 21/61* (2013.01); *G01N 33/0036* (2013.01); *G01N 2201/0636* (2013.01); *G01N 2201/06113* (2013.01)

(58) Field of Classification Search
CPC ........... G01N 21/3504; G01N 21/8507; G01N 21/05; G01N 15/14; G01N 2015/0046;
(Continued)

(56) References Cited

U.S. PATENT DOCUMENTS 3,960,500 A * 6/1976 Ross .................... G01N 1/2258
204/424
4,578,986 A * 4/1986 Navarre ............. G01N 33/0031
73/1.02
(Continued)

FOREIGN PATENT DOCUMENTS

EP    0243139 A    10/1987
JP    6312938 A    1/1988
(Continued)

OTHER PUBLICATIONS

International Search Report for International Application No. PCT/JP2015/077795 dated Oct. 30, 2015.
(Continued)

*Primary Examiner* — Taeho Jo
(74) *Attorney, Agent, or Firm* — Brooks Kushman P.C.

(57) ABSTRACT

A gas analysis device includes a probe tube, a flange, an optical system member, and heaters. The probe tube includes an optical path through which measurement light is projected onto a prescribed measurement region of a sample gas flowing through a flue and/or is received from the measurement region. The flange is fixed to the outer periphery of the probe tube and is attached to a pipe side wall. The optical system member projects measurement light onto the sample gas S within the measurement region and/or receives measurement light from the measurement region. The heaters are disposed within the flange and heats the portion where the probe tube and flange are fixed to each other.

6 Claims, 4 Drawing Sheets

(51) Int. Cl.
*G01N 21/61* (2006.01)
*G01N 33/00* (2006.01)

(58) Field of Classification Search
CPC . G01N 2030/3053; G01N 2201/06113; G01N 2201/068; G01N 30/30
USPC ........................................................ 250/352
See application file for complete search history.

(56) References Cited

U.S. PATENT DOCUMENTS

| | | | | |
|---|---|---|---|---|
| 4,827,134 | A * | 5/1989 | Willner | G01N 30/80 250/341.6 |
| 5,163,332 | A * | 11/1992 | Wong | G08B 29/20 250/338.5 |
| 5,241,262 | A * | 8/1993 | Guthrie | G01N 15/12 164/4.1 |
| 5,781,306 | A * | 7/1998 | Hartig | G01N 21/31 250/373 |
| 6,120,664 | A * | 9/2000 | Patel | G01N 27/4077 204/424 |
| 7,111,503 | B2 * | 9/2006 | Brumboiu | B01D 61/18 73/64.56 |
| 2002/0146351 | A1 * | 10/2002 | Lancelin | G01N 15/0255 422/94 |
| 2003/0090665 | A1 * | 5/2003 | Kaufmann | G01N 21/05 356/438 |
| 2003/0090666 | A1 | 5/2003 | Kaufmann | |
| 2007/0000338 | A1 * | 1/2007 | Brumboiu | B01D 61/18 73/866.5 |
| 2008/0314748 | A1 * | 12/2008 | Yamauchi | G01N 27/4067 204/431 |
| 2013/0161544 | A1 * | 6/2013 | Ohnishi | G01N 21/85 250/564 |

FOREIGN PATENT DOCUMENTS

| JP | 03154852 A | 7/1991 |
|---|---|---|
| JP | 06066691 A | 3/1994 |
| JP | 2013164336 A | 8/2013 |

OTHER PUBLICATIONS

International Preliminary Report on Patentability for International Application No. PCT/JP2015/077795 dated Apr. 18, 2017.

* cited by examiner

GAS ANALYSIS DEVICE

CROSS-REFERENCE TO RELATED APPLICATIONS

This application is a continuation of PCT Application Serial No. PCT/JP2015/077795 filed Sep. 30, 2015, which claims priority to Japanese Application No. 2014-212310 filed Oct. 17, 2014, the disclosure of which is hereby incorporated in its entirety by reference herein.

TECHNICAL FIELD

The present disclosure relates to a gas analysis device, and in particular to a gas analysis device which projects measurement light onto a sample gas flowing through a pipe and receives it in order to analyze the concentration of a predetermined component.

BACKGROUND

In flue gases discharged from boilers and incinerators which combust coal and heavy oil, components such as sulfur oxides (SOx), nitrogen oxides (NOx), carbon dioxide ($CO_2$), carbon monoxide (CO), HCl, $NH_3$, and other components are contained.

One example of gas analysis devices for analyzing the amounts of the components contained in a gas is as follows. The device includes a probe arranged so as to intersect a gas flow path in a pipe, and measurement light emitted from a light source to the gas is reflected by a reflector arranged at the tip of the probe, so that the concentration of a component of the sample gas is analyzed based on the information of the reflected measurement light (for example, refer to patent document 1).

The probe of the gas analysis device is in the form of a hollow pipe through which the measurement light passes. The probe is arranged so as to intersect with the gas flow path in the flue. An annular flange is fixed on the probe, and the flange is attached to a side wall of the pipe.

At the proximal end of the probe, a light emitting unit which emits measurement light into the probe, and a photodetector for receiving the reflected light are provided. At the tip of the probe, a reflector is provided for reflecting the measurement light from the light emitting unit to the photo detector side.

In the above gas analyzing device, gas in flue is introduced into the probe by diffusion, and the measurement light emitted from the light emitting unit and reflected by the reflector is received by the photo detector, so that components in the gas can be analyzed based on the characteristics of this measurement light.

SUMMARY

Technical Problem

The inventors had examined such a conventional gas analyzer, and newly focused on the following problem. In the gas analyzer, the probe is heated by flue gas at a high temperature (for example, 100° C. to 400° C.), but a base of the probe and a fixed portion of the flange are not sufficiently heated (for example, lower than 100° C.). There is also the problem that the components contained in the gas (particularly acid components have great influence) cause the dew point to be increased, which causes condensation at the above-mentioned portions, resulting in corrosion of the portions. When the base of the probe is corroded, the straightness of the probe is adversely affected, which may lead to the problem of deviated optical axis. Therefore, it is important to address the aforementioned corrosion problem for the purpose of ensuring analysis accuracy in the gas analyzer.

Technical Solution

A plurality of aspects for solving the problems will be described below. These aspects can be combined optionally as necessary.

A gas analysis device according to one aspect of the present invention includes a tubular member, an annular flange, an optical system member, and a heater. The tubular member includes an optical path through which measurement light is projected onto a predetermined measurement region of a sample gas flowing through a pipe and/or is received from the measurement region. The annular flange is fixed to an outer periphery of the tubular member, and is mounted on a side wall of the pipe. The optical system member is configured to project the measurement light onto the sample gas within the measurement region and/or receive the measurement light from the measurement region. The heater is disposed within the annular flange and is configured to heat a fixed portion between the tubular member and the annular flange.

In this gas analysis device, the fixed portion between the tubular member and the annular flange is heated by the heater. In particular, the heater is disposed within the annular flange, and therefore the heating effects in the fixed portion between the tubular member and the annular flange are high, regardless of the thermal conductivity of the flange itself. As a result, the temperature can be easily increased to a desired temperature. Therefore, dew condensation in the fixed portion between the tubular member and the annular flange is unlikely to occur, thereby preventing corrosion.

The gas analysis device may further include a heat insulating member covering the heater and the annular flange to shut the heater and the annular flange from the outside air.

In this case, heat is prevented from dissipating from the probe and the annular flange. Therefore, the heating efficiency using the heater is improved.

The gas analysis device may further include a heat insulating connection structure disposed in the tubular member between the annular flange and the optical system member. The heat insulating connection structure connects the annular flange and the optical system member while insulating heat between the annular flange and the optical system member.

In this case, heat is unlikely to be transferred from the probe and the annular flange toward the optical system member. Thus, the optical system member is not exposed to high temperatures.

According to one aspect of the present invention, a heater is disposed in a hole formed on the outer peripheral surface of the annular flange. This facilitates mounting of the heater.

According to one aspect of the present invention, the heater is attachable/detachable to/from the hole. This allows easy replacement operation of the heater.

According to one aspect of the present invention, a plurality of heaters are disposed and spaced away from each other in the circumferential direction with respect to the annular flange. Accordingly, the heater can heat the annular flange entirely.

According to one aspect of the present invention, a probe tube and a flange are fixed by welding, and a heater directly heats the weld. Accordingly, even if the corrosion resistance of the weld is lowered due to a change in ratio of components during welding, the weld is prevented from corrosion because of directly heating the weld.

Advantageous Effects

In the gas analysis device according to one or more embodiments of the present invention, in a gas analysis device for measuring a concentration of a gas flowing through a pipe by an optical measurement system, a probe attached to a pipe side wall via a flange is unlikely to be corroded. Embodiments of the present invention prevent the corrosion of a base and flange of a probe attached to a pipe side wall in a gas analysis device for using an optical measurement system to measure the concentration of gas flowing through a pipe.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

1. First Embodiment (1) Overall Configuration

Figure 1:
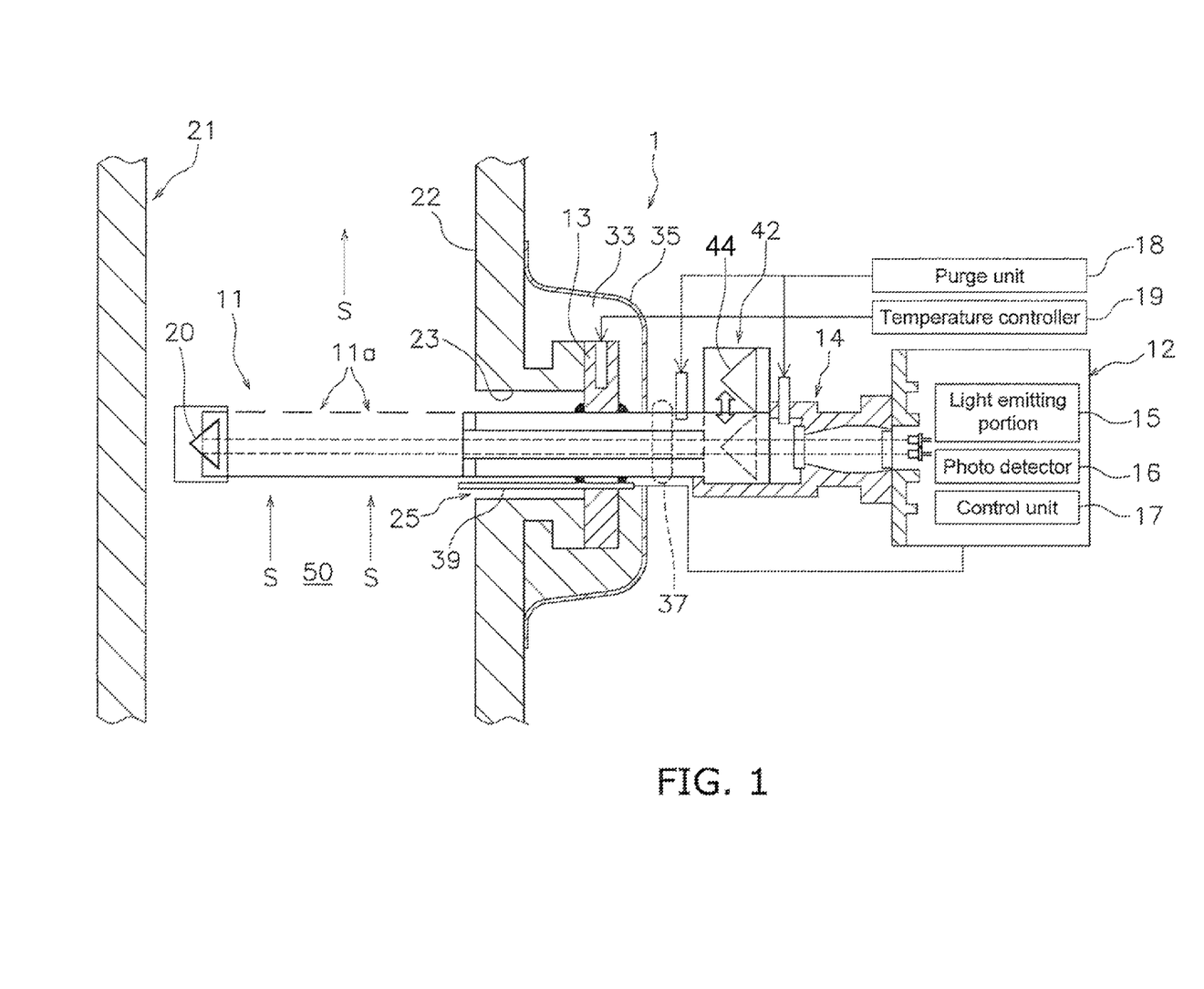
FIG. 1 is a schematic cross-sectional view of a gas analysis device of the first embodiment.
Figure 2:
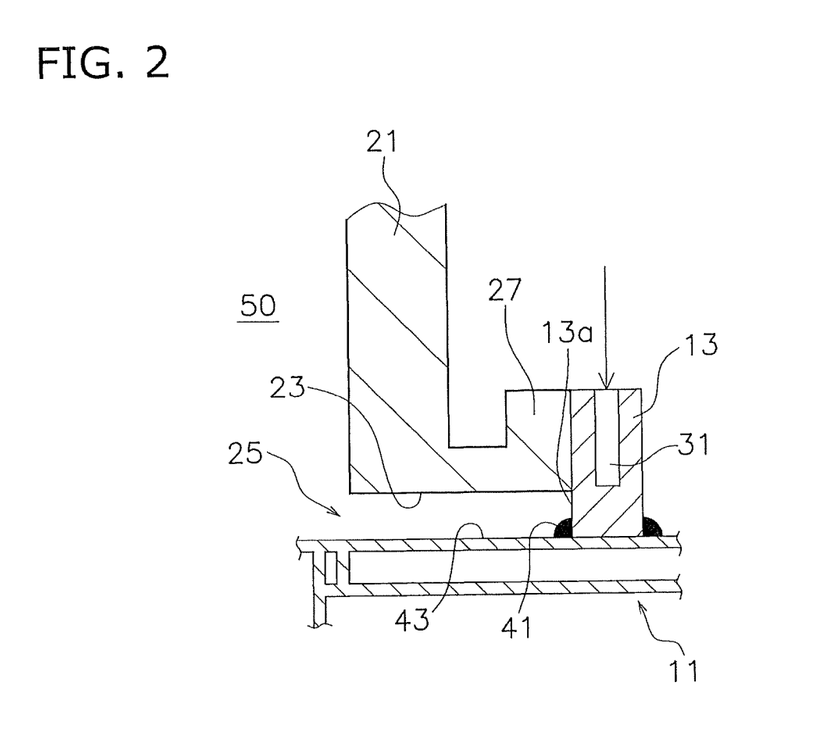
FIG. 2 is a partially enlarged view of FIG. 1.

FIG. 1 is a schematic cross-sectional view of a gas analysis device of the first embodiment. FIG. 2 is a partially enlarged view of FIG. 1.

A gas analysis device 1 is a device for analyzing a sample gas S, the sample gas S flowing through a flue 50 and being introduced into the gas analysis device 1 by diffusion. The flue 50 is composed of a pipe.

The gas analysis device 1 mainly includes a probe tube 11 (an example of the tubular member), an analysis unit 12, and a flange 13.

The analysis unit 12 includes a light emitting unit 15, a photo detector 16 (an example of the optical system member), and a control unit 17.

The light emitting unit 15 is a light source for emitting a laser beam which serves as a measurement light through a light guiding pipe 14 and the probe tube 11 to a gas to be measured. The light emitting unit 15 may be configured with an infrared laser oscillator for irradiating a light in a predetermined wavelength region with a high linearity.

The photo detector 16 is a photodetector for receiving the measurement light which is incident through the gas to be measured in the flue.

The control unit 17 controls the emission of the laser beam from the light emitting unit 15, and performs a component analysis of the gas to be measured based on the measurement light received by the photo detector 16.

The probe tube 11 is formed in a hollow cylindrical shape, and is disposed perpendicularly to the sample gas S in the flue 50 formed in the inside of a pipe side wall 21 of the pipe. The material of the probe tube 11 used is preferably a metal material such as stainless steel, which has heat resistance and corrosion resistance.

In the measurement region of the probe tube 11, an opening 11a is provided on the downstream side of the sample gas S for introducing the gas into the probe tube 11. The number, position, and shape of the opening 11a are not particularly limited.

At the tip of the probe tube 11, a reflector 20 for reflecting the measurement light emitted from the light emitting unit 15 of the analytical unit 12 is provided. The reflector 20 reflects the measurement light emitted from the light emitting unit 15 to the side of the photo detector 16, and can be composed of a corner cube.

The flange 13 is a member for fixing the probe tube 11 into the pipe side wall 21. The flange 13 is, as shown in FIG. 2, fixed to the probe tube 11 by a weld 41 (FIG. 2). The flange 13 is made of, for example, stainless steel.

The gas analysis device 1 is attached to a mounting hole 23 of the pipe side wall 21. More specifically, as shown in FIG. 2, a mounting portion 27 is provided on the analysis unit 12 side of the mounting hole 23, and the aforementioned flange 13 is bolted to the mounting portion 27. With the above configuration, an annular space 25 is ensured between an outer peripheral surface 43 of the inner circumferential surface of the mounting hole 23 and the probe tube 11 (in particular, the base portion to which the flange 13 is fixed), and the sample gas S from the flue 50 flows into the space 25 in the annular space. As a result, the outer peripheral surface 43 of the probe tube 11 (in particular, the base to which the flange 13 is fixed) and a main surface 13a of the inner circumferential side of the flange 13, the weld 41 on the flue side are exposed to the sample gas S.

In the present embodiment, a drive mechanism 42 including a second reflector 44 is provided on the analytical unit 12 side. The second reflector 44 is for reflecting the measurement light from the photo detector 16, and is, for example, a corner cube. In the space between the analysis unit 12 and the second reflector 44, a known gas, span gas, and zero gas can be charged. The drive mechanism 42 includes a spring and an air cylinder. When performing the analysis of component concentrations, the drive mechanism 42 removes the second reflector 44 from the optical path, while when performing correction or calibration, it places the second reflector 44 on the optical path.

(2) Corrosion Problem and Heater

In prior art, the temperature of the sample gas S in the flue 50 is 100° C. to 400° C., but the temperature of the sample gas is lowered in the space 25, which causes dew condensation. The condensed moisture is deposited on the outer peripheral surface 43 of the probe tube 11, the main surface 13a on the inner circumferential side of the flange 13, and the weld 41 on the flue side. Since the flue gas contains acid, corrosion occurs in the portions where dew condensation has occurred. The gases which are the main cause of corrosion are hydrogen chloride (HCl), sulfur oxides ($SO_X$), and nitrogen oxides ($NO_X$).

Figure 3:
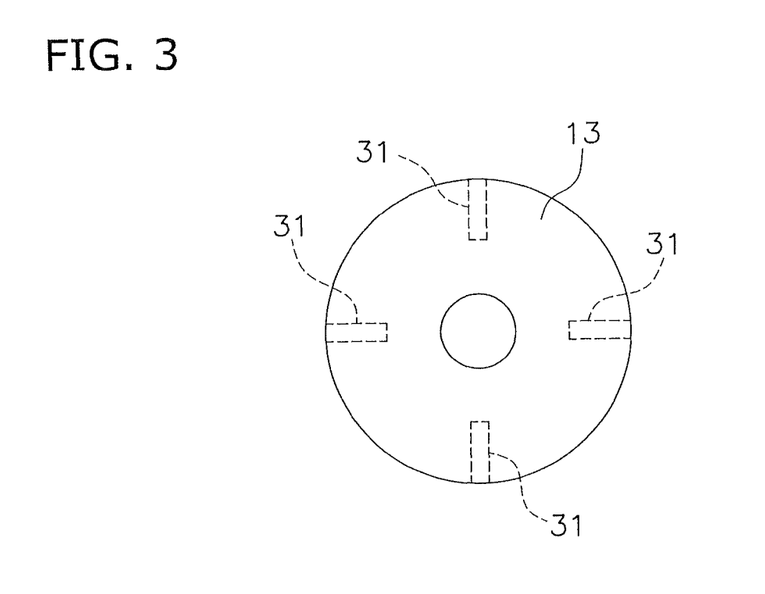
FIG. 3 is a plan view of a flange portion.

Therefore, in this embodiment, the provision of the heaters 31 prevents dew condensation in the space 25 so that corrosion of the above-mentioned portions is prevented. The heaters 31 are attached directly to the flange 13. More specifically, the heaters 31 are mounted within the flange 13. More specifically, as shown in FIGS. 2 and 3, the heaters 31 are mounted in holes extending from the outer peripheral surface toward the center of the flange 13. There are a multiple number of the heaters 31, and the number is four in this embodiment. The heaters 31 are arranged at regular intervals in the circumferential direction. In this embodiment, the heaters 31 are cartridge heaters.

The heaters 31 are controlled by a temperature controller 19 in FIG. 1. The temperature controller 19 is a device for controlling the heaters 31 so as to avoid dew condensation in the above-mentioned portions based on various conditions. The temperature controller 19 controls electric power supplied to the heaters 31, and includes a control unit for controlling the output of the heater 31. The controlled temperature is appropriately set in accordance with the exhaust gas conditions and the site environment. The site environment is, for example, a temperature of exhaust gas, concentration of coexisting water vapor, species of coexisting acidic and basic gases, ambient temperature, and the form of the target duct.

Furthermore, in the space 25, as shown in FIG. 1, a temperature sensor 39 for detecting the temperature in the flue 50 is provided. The temperature controller 19 may control operation based on a signal transmitted from the temperature sensor 39.

Purge units 18 for supplying purge gas to the measurement region are provided at both ends of the probe tube 11. The purge gas is for preventing the optical system members such as the light emitting unit 15, the photo detector 16, and the reflector 20 from being exposed to the sample gas. The purge gas is supplied to the probe tube 11 through the light guiding pipe 14. Furthermore, the purge gas is supplied to the tip of the probe tube 11 by a purge gas supply pipe (not shown) disposed in the light guiding pipe 14 and the probe tube 11.

When performing a catoptric measurement, an analysis is performed based on the measurement light having emitted from the light emitting unit 15, passed through the inside of the probe tube 11, reflected by the reflector 20, passed through the inside of the probe tube 11 again and received by the photo detector 16.

(3) Details of Heaters

The heaters 31 are mounted in the flange 13 to heat the fixed portion of the probe tube 11 and the flange 13. Since the heaters 31 are mounted inside the flange 13, their heating effects in the above-mentioned fixed portion are high. As a result, the temperature can be easily increased to a desired temperature. Therefore dew condensation in the fixed portion of the probe tube 11 and the flange 13 is unlikely to occur, thereby preventing corrosion.

Since the target to be directly heated by the heater 31 is the inside of the flange 13, the temperature of the portion in the vicinity of the flange 13 can be easily increased even if the flange is made of a material with a low thermal conductivity such as stainless steel. In other words, reduced power consumption is achieved. In addition, since the heaters 31 are attached directly to the flange 13, the heating structure does not occupy a large space in the gas analysis device 1.

As a result, the linearity of the optical axis in the probe tube 11 is maintained, so that it is possible to perform accurate gas analysis over a long period of time.

In particular, the heaters 31 directly heat the weld 41, which is a fixed portion of the probe tube 11 and the flange 13, and therefore it is highly effective in preventing corrosion. In general, the weld is likely to have lower corrosion resistance due to changes in the ratio of components during welding. In this embodiment, the weld 41 is heated so that it is unlikely to be corroded even in such a case. As a matter of course, the heaters 31 are also effective in preventing corrosion in portions other than the weld 41. Furthermore, since the heaters 31 directly heat the weld 41, the size of the heating structure is reduced.

For example, when the temperature of the flue gas is low, the concentrations of the acid components such as HCl, $SO_x$, and $NO_x$ coexisting in the exhaust gas are high, and a rise in the dew point is enhanced. It is particularly problematic in the case where the ambient temperature is low and the target duct has an R portion.

In particular, since the heaters 31 are installed in the flange 13, the heating efficiency of the flange 13 by the heaters 31 is improved. This is because the heat from the heaters 31 is unlikely to dissipate to the outside of the flange 13. In the present embodiment, the heaters 31 can be attached by simply making holes in the flange 13, and it is therefore unnecessary to provide a special new structure. In addition, since the heaters 31 can be easily inserted into and removed from the holes on the flange 13, they can be easily replaced.

The type, number, installation method, and installation position of the heaters are not particularly limited. The number of the heater may be singular. When the number of the heaters is plural, the arrangement position relationship among themselves and the respective control conditions of the heaters can be set appropriately. However, the heaters are preferably provided in positions closer to the center of the flange. This is for sufficiently heating the weld 41.

The target temperature of the space 25 by the heaters 31 is not particularly limited as long as the above effects can be obtained, and is, for example, 100° C. or higher.

The heaters 31 may be configured to perform heating only when the incinerator is in operation, or may be configured to perform heating even when the incinerator is out of operation and the sample gas S is not flowing through the flue 50.

(4) Heat Insulating Member

The gas analysis device 1 further includes a heat insulating member 33. The heat insulating member 33 is a covering member for shutting the heaters 31 and the flange 13 from the outside air. As shown in FIG. 1, the heat insulating member 33 covers the heaters 31 and flanges 13. Furthermore, the heat insulating member 33 also covers the mounting portion 27. The heat insulating member 33 is, for example, silicone rubber. The heat insulating member 33 is covered with a cover 35.

The heat insulating member 33 increases the heating effects in the flange 13. Thus, the flange 13 can be sufficiently heated while electric power supplied to the heaters 31 is kept low.

The material, amount, shape, and arrangement position of the heat insulating member are not limited to those in the above embodiment.

Furthermore, the heat insulating member may be omitted.

(5) Heat Insulating Connection Structure

The gas analysis device 1 further includes a heat insulating connection structure 37. The heat insulating connection structure 37 is disposed between the flange 13 and the light emitting unit 15 and the photo detector 16 in the probe tube 11, and is configured to connect the two sides while insulating heat between the two sides. More specifically, the heat insulating connection structure 37 is disposed between the flange 13 and the drive mechanism 41.

The heat insulating connection structure 37 is, for example, a structure for preventing contact of metals in a position where cylindrical members are connected with each other, and is realized by, for example, a member made of a glass epoxy resin, and O-ring or the like. The heat insulating connection structure 37 prevents the heat generated by the heaters 31 from being transmitted toward the light emitting unit 15 and the photo detector 16. In particular, the light emitting unit 15 and the photo detector 16 have low heat resistance, and it is therefore important to thermally shut the components from the controlled high temperature. Furthermore, the drive mechanism 42 is very sensitive to heat expansion, where the heat insulating connection by the heat insulating connection structure 37 is effective for suppressing heat expansion.

(6) Experimental Results

The inventors of the present disclosure had conducted an experiment on the occurrence and prevention of corrosion by using the above-described gas analysis device 1 over several months. In a conventional gas analysis device which employs no heater, the probe tube and flange were corroded within one month, and the metallic luster on the surfaces thereof disappeared. In contrast, in the gas analysis device using heaters, no corrosion occurred in the respective members even after 9 months, and the metallic luster on the surfaces thereof was maintained.

2. Second Embodiment

In the first embodiment, the flange fixed to the probe tube is fixed directly to the pipe side wall, but the mounting structure of the flange is not particularly limited.

Figure 4:
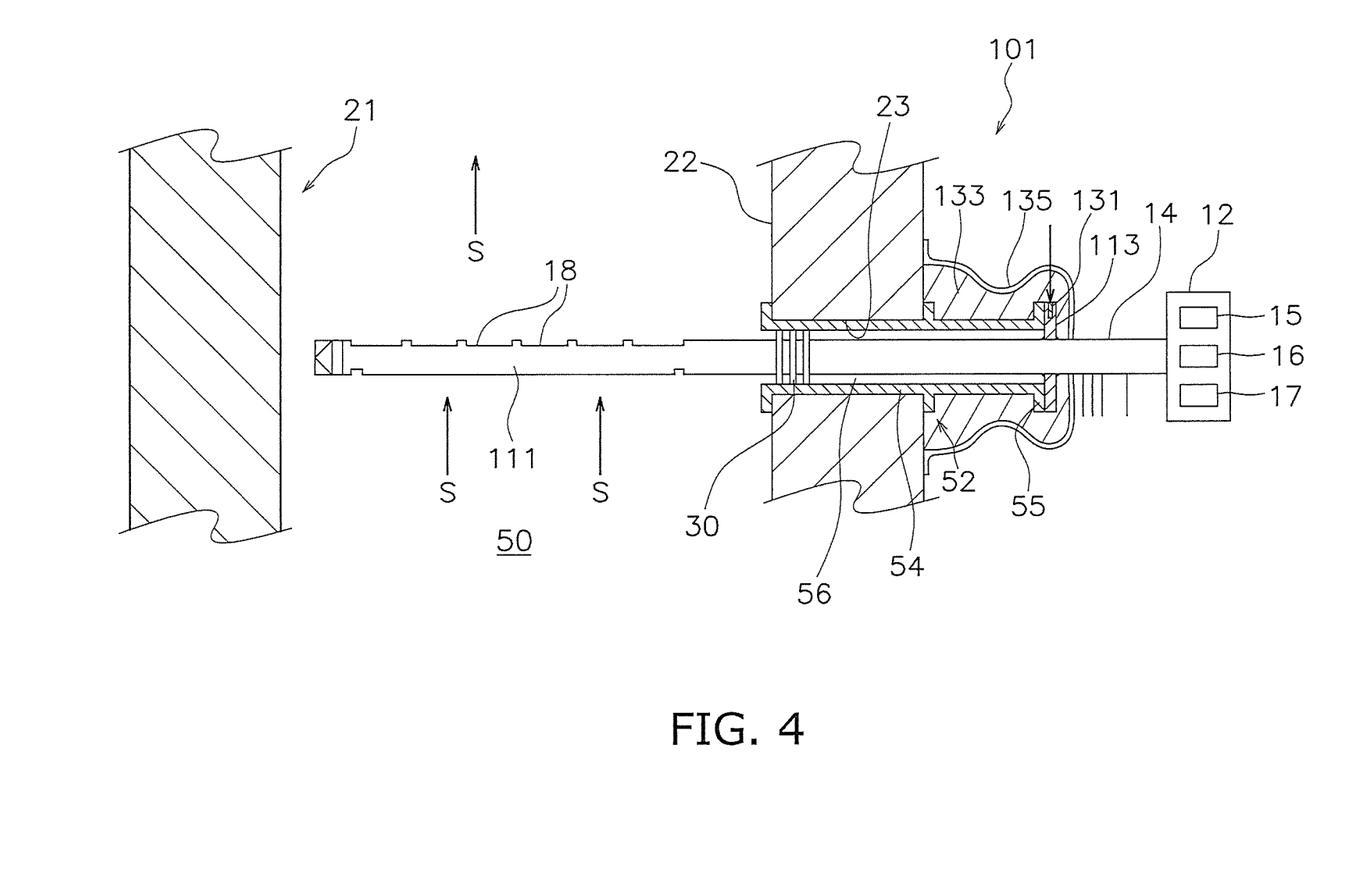
FIG. 4 is a schematic cross-sectional view of a gas analysis device of the second embodiment.
Figure 5:
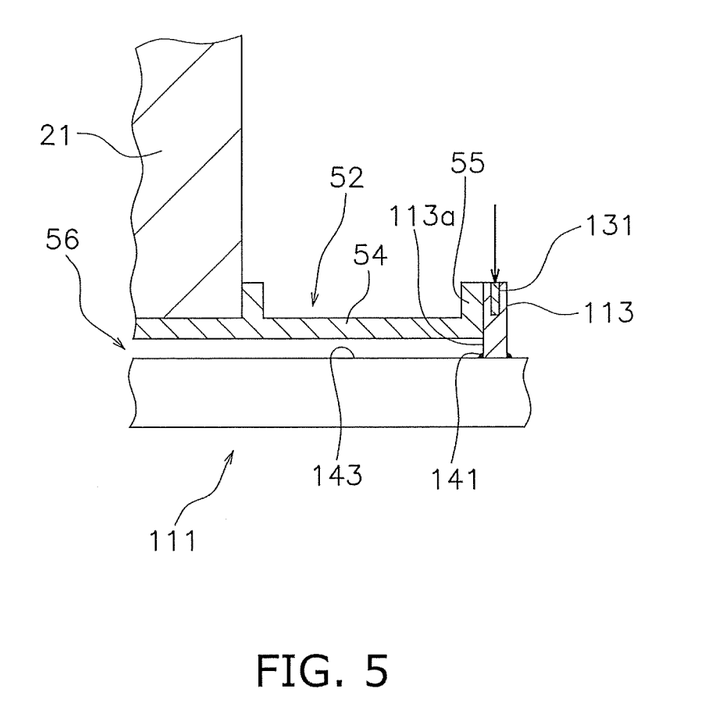
FIG. 5 is a partially enlarged view of FIG. 4.

With reference to FIGS. 4 and 5, another embodiment of the mounting structure of the flange will be described.

A gas analysis device 101 is attached to an attachment portion 52 of a pipe side wall 21 which is a component of a flue 50. The attachment portion 52 is, for example, composed of an installation pipe 54 attached to a mounting hole 23 of the pipe side wall 21.

The installation pipe 54 is a cylindrical member having an inner diameter larger than the outer diameter of the probe tube 111 of the gas analysis device 101, and is fixed to the pipe side wall 21 by welding, screwing, or other means.

Furthermore, the installation pipe 54 is provided with a mounting flange 55 for fixing the gas analysis device 101, and a flange 113 of the gas analysis device 101 is welded or screwed to the mounting flange 55, whereby the gas analysis device 101 is indirectly fixed to the pipe side wall 21. Between a probe tube 111 and the installation pipe 54, a space 56 is ensured.

A shielding plate 30 is provided between the thus-configured probe tube 111 and installation pipe 54 so that part of the sample gas S flowing through the flue 50 is prevented from flowing into the space 56. The shielding plate 30 is positioned in the vicinity of the inner surface 22 of the pipe side wall 21. Since the shielding plate 30 is provided on the side of the flue 50 in such a manner, the sample gas S is prevented from flowing into the space 56. The shielding plate 30 is a disc-shaped member fixed to the outer peripheral surface of the probe tube 111, and its outer peripheral edge is in the vicinity of or in contact with the inner peripheral surface of the installation pipe 54. In the case where they are in the vicinity, it is preferable that the gap therebetween is small in terms of shutting out the sample gas S. In the case where they are in contact, the space 56 is shielded, so that the shutting effects of the sample gas is increased.

In the example illustrated, three shielding plates 30 are disposed at predetermined intervals along the length of the probe tube 111. Since the plurality of shielding plates 30 is arranged with gaps in the axial direction of the probe tube 111, the sample gas S is unlikely to flow into the space 56.

In addition to the shielding plate 30, purge air may be supplied into the space 56 as in the third embodiment to be described later, so that the sample gas S can be prevented from flowing into the space 56 more effectively.

With the above structure, as shown in FIG. 5, an annular space 56 is ensured between the inner peripheral surface of the installation pipe 54 and the outer peripheral surface 143 of the probe tube 111 (in particular, the base to which the flange 113 is fixed), and the sample gas S restrictedly flows from the flue 50 into the annular space 56. As a result, the outer peripheral surface 143 of the probe tube 111 (in particular, the base to which the flange 113 is fixed) and a main surface 113a on the inner circumferential side of the flange 113, and the weld 141 on the flue side are exposed to the sample gas.

In the present embodiment, the provision of the heaters 31 prevents dew condensation in the space 56 so that the above-mentioned portions is prevented from being corroded. The heaters 131 are attached directly to the flange 113. More specifically, the heater 131 is mounted in the inside of the flange 113. The heaters 131 are, more specifically, as shown in FIG. 5, mounted in holes extending from the outer peripheral surface toward the center of the flange 113. The type, number, arrangement position, and control means of heaters 131 are the same as those in the first embodiment.

The gas analysis device 101 further includes, as shown in FIG. 4, a heat insulating member 133. The heat insulating member 133 is a member for covering the heater 131 and flange 113 to shut out these components from the outside air. As shown in FIG. 4, the heat insulating member 133 covers the heater 131 and flange 113. In addition, the heat insulating member 133 also covers part of the installation pipe 54. The heat insulating member 133 is covered by a cover 135.

The heat insulating member 133 increases the heat keeping effects in the flange 113. Therefore, the flange 113 can be sufficiently heated while electric power supplied to the heater 131 is kept low.

3. Third Embodiment

As another embodiment, in addition to the configurations of the first embodiment and second embodiment, such a configuration that prevents exhaust gas from entering into the above-mentioned space may be provided by supplying purge gas to the space between the probe tube and the inner peripheral surface of the wall. This makes the above-descried corrosion less likely to occur.

Supply of the purge gas may be performed simultaneously with the heating of the heater, or may be performed when heating by the heater is not performed, for example, during installation of the gas analyzing device.

The dew point of the sample gas S can be also lowered by diluting the sample gas S with a purge gas.

4. Other Embodiments

The plurality of embodiments has been described above, but the present invention is not limited to the above embodiments, and various modifications may be made unless they deviate from the purpose of the present invention. In particular, the plurality of embodiments and variations stated herein can be combined optionally as necessary.

For example, the tubular member is not limited to the probe tube. The tubular member may be any member as long as it includes an optical path through which the measurement light is projected to the predetermined measurement region of the sample gas flowing through the pipe and/or is received from the measurement region.

The gas analysis device is not limited to one that performs reflective optical measurement, and may be one that performs transmissive optical measurement.

The shape of the probe tube is not limited to the above-described configuration. Its shape may be a hollow configuration through which the measurement light can pass through, and its cross section may be polygonal, oval, or any shape which is a combination of the same.

Although the target of analysis of the gas analysis device of the above-mentioned embodiment is combustion exhaust gas, but it may be various process gases and the like.

INDUSTRIAL APPLICABILITY

The present invention can be widely applied to gas analysis devices for analyzing the concentration of a predetermined component by emitting and receiving the measurement light in a sample gas flowing through a pipe.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:
1. A gas analysis device comprising:
a tubular member including an optical path through which measurement light is projected to a predetermined measurement region of a sample gas flowing through a pipe and/or is received from the measurement region;
an annular flange fixed to an outer periphery of the tubular member and mounted on a side wall of the pipe;
an optical system member configured to project the measurement light to the sample gas in the measurement region and/or receive the measurement light from the measurement region; and
a heater attached directly to the annular flange, configured to heat a weld portion between the tubular member and the annular flange.
2. The gas analysis device according to claim 1, further comprising a heat insulating member covering the heater and the annular flange to shut the heater and the annular flange from outside air.
3. The gas analysis device according to claim 1, further comprising a heat insulating connection structure disposed in the tubular member between the annular flange and the optical system member, and connecting the annular flange and the optical system member while insulating heat between the annular flange and the optical system member.
4. The gas analysis device according to claim 2, further comprising a heat insulating connection structure disposed in the tubular member between the annular flange and the optical system member, and connecting the annular flange and the optical system member while insulating heat between the annular flange and the optical system member.
5. The gas analysis device according to claim 1, wherein the heater is attached directly to an outer periphery of the annular flange.
6. The gas analysis device according to claim 1, wherein an outer circumferential surface of the tubular member is smaller than an inner circumferential surface of a mounting hole in the sidewall of the pipe to define a space extending from an inside of the pipe to an inner periphery of the flange fixed to the tubular member.

* * * * *